(12) United States Patent
Tricca et al.

(10) Patent No.: US 10,857,075 B2
(45) Date of Patent: Dec. 8, 2020

(54) WET WIPER ARTICLES AND METHODS FOR CLEANING REMOVABLE DENTAL APPLIANCES

(71) Applicant: Oral Health Technologies, LLC, Danville, CA (US)

(72) Inventors: Robert Eugene Tricca, Danville, CA (US); Malia Mueller Smith, Mountain View, CA (US)

(73) Assignee: Oral Health Technologies, LLC, Danville, CA (US)

(*) Notice: Subject to any disclaimer, the term of this patent is extended or adjusted under 35 U.S.C. 154(b) by 0 days.

(21) Appl. No.: 14/529,013

(22) Filed: Oct. 30, 2014

(65) Prior Publication Data

US 2015/0053235 A1 Feb. 26, 2015

Related U.S. Application Data

(60) Continuation of application No. 14/150,008, filed on Jan. 8, 2014, which is a division of application No. 11/879,285, filed on Jul. 17, 2007, now Pat. No. 8,632,636.

(60) Provisional application No. 60/831,713, filed on Jul. 18, 2006.

(51) Int. Cl.

| | |
|---|---|
| *A61K 8/02* | (2006.01) |
| *C11D 3/20* | (2006.01) |
| *C11D 3/382* | (2006.01) |
| *C11D 7/26* | (2006.01) |
| *C11D 7/44* | (2006.01) |
| *C11D 11/00* | (2006.01) |
| *A61K 8/34* | (2006.01) |
| *A61Q 11/02* | (2006.01) |
| *A61K 8/92* | (2006.01) |
| *A61K 8/9789* | (2017.01) |
| *C11D 1/83* | (2006.01) |
| *C11D 3/43* | (2006.01) |
| *C11D 3/48* | (2006.01) |
| *C11D 17/04* | (2006.01) |
| *A61K 8/27* | (2006.01) |
| *A61Q 11/00* | (2006.01) |
| *C11D 3/00* | (2006.01) |
| *C11D 3/04* | (2006.01) |
| *B08B 1/00* | (2006.01) |

(52) U.S. Cl.
CPC .............. *A61K 8/0208* (2013.01); *A61K 8/27* (2013.01); *A61K 8/34* (2013.01); *A61K 8/922* (2013.01); *A61K 8/9789* (2017.08); *A61Q 11/00* (2013.01); *A61Q 11/02* (2013.01); *C11D 1/83* (2013.01); *C11D 3/0068* (2013.01); *C11D 3/046* (2013.01); *C11D 3/201* (2013.01); *C11D 3/382* (2013.01); *C11D 3/43* (2013.01); *C11D 3/48* (2013.01); *C11D 7/261* (2013.01); *C11D 7/44* (2013.01); *C11D 11/0023* (2013.01); *C11D 17/049* (2013.01); *B08B 1/006* (2013.01)

(58) Field of Classification Search
CPC .......... A61K 8/0208; A61K 8/27; A61K 8/97; C11D 17/049; C11D 1/83; C11D 3/046; C11D 3/48; C11D 3/0068; A61Q 11/00
USPC ......................... 134/93; 15/104.93; 510/116
See application file for complete search history.

(56) References Cited

U.S. PATENT DOCUMENTS

| | | | |
|---|---|---|---|
| 5,041,236 A | * | 8/1991 | Carpenter .............. A01N 63/00 424/94.61 |
| 5,320,772 A | | 6/1994 | Tricca |
| 5,498,295 A | | 3/1996 | Murch et al. |
| 5,500,048 A | | 3/1996 | Murch et al. |
| 5,500,143 A | | 3/1996 | Murch et al. |
| 5,503,764 A | | 4/1996 | Murch et al. |
| 5,549,758 A | | 8/1996 | Murch et al. |
| 5,705,461 A | | 1/1998 | Murch et al. |
| 5,749,924 A | | 5/1998 | Murch et al. |
| 5,849,678 A | | 12/1998 | Murch et al. |
| 5,879,470 A | | 3/1999 | Murch et al. |
| 5,914,302 A | | 6/1999 | Murch et al. |
| 5,932,527 A | | 8/1999 | Roselle et al. |
| 5,939,050 A | | 8/1999 | Iyler et al. |
| 5,965,499 A | | 10/1999 | Murch et al. |
| 5,972,857 A | | 10/1999 | Roselle et al. |
| 5,997,654 A | | 12/1999 | Murch et al. |
| 6,345,634 B1 | | 2/2002 | Murch et al. |
| 6,367,488 B1 | | 4/2002 | Murch et al. |

(Continued)

FOREIGN PATENT DOCUMENTS

| | | |
|---|---|---|
| GB | 2224425 A | 5/1990 |
| WO | 97/01290 A2 | 1/1997 |

(Continued)

OTHER PUBLICATIONS

U.S. Appl. No. 11/879,285, Notice of Allowance, dated Sep. 16, 2013, 10 pages.

(Continued)

*Primary Examiner* — Eric W Golightly
(74) *Attorney, Agent, or Firm* — Kilpatrick Townsend & Stockton LLP

(57) ABSTRACT

A wet wiper for cleaning accumulated oral debris from removable dental appliances. The wet wiper comprises (a) a water insoluble substrate; and (b) a physiologically acceptable cleansing composition, said cleansing composition comprising: a solution of water and a flavorant, wherein said water is up to about 97% by weight of said cleansing composition; and said flavorant is about 0.001% to about 5% by weight of said cleansing composition. Methods for cleaning removable dental appliances are also provided, such methods comprising the step of contacting, for a time sufficient to reduce oral debris, the removable dental appliances, with a wet wiper of the present invention.

2 Claims, No Drawings

(56) References Cited

U.S. PATENT DOCUMENTS

| | | |
|---|---|---|
| 6,557,568 B1 | 5/2003 | Murch et al. |
| 6,662,813 B1 | 12/2003 | Murch et al. |
| 6,821,940 B2 | 11/2004 | Bullock et al. |
| 6,831,050 B2 | 12/2004 | Murch et al. |
| 8,632,636 B1 | 1/2014 | Tricca |
| 2001/0041665 A1 | 11/2001 | Severns et al. |
| 2003/0216479 A1 | 11/2003 | Huang et al. |
| 2004/0106994 A1 | 6/2004 | De Maeztus Martinez et al. |
| 2004/0156796 A1 | 8/2004 | Morgan et al. |
| 2004/0214127 A1 | 10/2004 | Kubo et al. |
| 2005/0048007 A1 | 3/2005 | Ruggles |
| 2014/0128304 A1 | 5/2014 | Tricca et al. |

FOREIGN PATENT DOCUMENTS

| | | |
|---|---|---|
| WO | 98/18352 A1 | 5/1998 |
| WO | 98/50518 A1 | 11/1998 |
| WO | 98/56889 A1 | 12/1998 |
| WO | 99/00025 A1 | 1/1999 |
| WO | 99/00026 A1 | 1/1999 |
| WO | 2005/037972 A1 | 4/2005 |

OTHER PUBLICATIONS

U.S. Appl. No. 11/879,285, Restriction Requirement, dated Nov. 17, 2009, 7 pages.

U.S. Appl. No. 11/879,285, Non-Final Office Action, dated Apr. 8, 2010, 15 pages.

U.S. Appl. No. 11/879,285, Final Office Action, dated Dec. 7, 2010, 13 pages.

\* cited by examiner

WET WIPER ARTICLES AND METHODS FOR CLEANING REMOVABLE DENTAL APPLIANCES

CROSS-REFERENCES TO RELATED APPLICATIONS

This application is a continuation of application Ser. No. 14/150,008, filed Jan. 8, 2014, now U.S. Pat. No. 9,937,108, issued Apr. 10, 2018, which is a division of application Ser. No. 11/879,285, filed Jul. 17, 2007, now U.S. Pat. No. 8,632,636, issued Jan. 21, 2014, which claims the benefit of U.S. Provisional Patent Application No. 60/831,713, filed Jul. 18, 2006, which are incorporated herein by reference in their entirety for all purposes.

BACKGROUND OF THE INVENTION

Removable dental appliances (hereinafter referred to as removable appliances) have been used since the early 1900's, and the category encompasses a wide variety which can be easily removed and re-inserted in the mouth, including those for function, expansion, orthodontics, retention, bruxism, protection of the hard and soft tissues and as a dental prosthesis. Examples of removable appliances include those used for orthodontic tooth positioning as in the system sold under the trademark, Invisalign;® retainers, of which Hawley and Essix-types are examples; as well as nightguards, mouthguards, biteguards, dentures, and removable partial dentures. Wear times of removable appliances vary. For example, some appliances, like sportsguards, are worn for only for a few hours and removed infrequently, while others, like aligners, are worn throughout the day and require more frequent removal and reinsertion for all meals, snacks and beverages. As removable appliances grow in popularity and use, the need for new intermittent oral care regimens, tailored to specific lifestyle considerations, is increasing.

The placement of removable appliances in the oral cavity leads to the accumulation of oral debris on the surfaces of the appliance and all of its parts. Typically, the major proportion of oral debris that accumulates on removable appliances is dental plaque which adheres tenaciously to the appliance surfaces and is not easily removed. Removal of dental plaque is important because it is a living structure containing organisms which have specific biochemical activities and metabolism and whose enhanced pathogenic potential constitutes a threat to oral health by stimulating disease processes such as dental caries and periodontal disease. In addition, the microorganisms contained in dental plaque have been implicated in the generation of objectionable mouth odors.

A problem with cleaning dental appliances is that it can be difficult, time-consuming, inconvenient, or even impossible at times, depending on how and when cleaning is needed. Two major approaches are generally recommended to patients cleaning removable appliances. One approach relies on mechanical devices, while the other approach utilizes chemical methods. In some instances, a combination of these approaches may actually be used.

The most familiar mechanical approach is with the use of a brush in the presence of either hot or cold water. A key disadvantage of this method is that it typically requires running water and a sink. Another disadvantage is that scrubbing the appliance with just water does little to kill pathogenic organisms that may be present on the appliance surfaces. A less common but more effective mechanical approach is through the use of a table-top ultrasonic cleaner; however, utilization is limited because the devices are bulky, not portable, and require a dedicated source of electrical power.

The other major approach recommended to patients for cleaning removable appliances is with the use of chemicals. The most common chemical method is soaking the removable appliance in a denture tablet solution. Certain mouthwash products are also used due to their more desirable odor, flavor and antibacterial claims of their manufacturers. Disadvantages of the chemical method, however, include soaking times, difficulty and inconveniences associated with the variety of auxiliary aids required, (e.g., water, soaking tub, sink) as well as possible discoloration of clear plastic appliances from some dyes within the chemical formulations.

Unclean removable appliances represent both esthetic and health concerns for the person using them. Despite the aforementioned approaches, there remains a need for a one-step cleaning regimen to efficiently and conveniently remove oral debris and malodors from removable appliances. As such, there is a need for a portable, disposable, wet wiper that can be used at any time, in any location, to clean and deliver mouth refreshment, without requiring additional auxiliary components like water or power. Such a product may be used several times a day, especially immediately after meals, in order to reduce accumulated oral debris and the return of oral malodor.

The art is replete with numerous wet wiper products for cleaning a variety of objects including glass, kitchen and bathroom countertops, furniture, sports equipment, skin, hair, food and food contact surfaces, yet the authors are unaware of any prior art covering the method of using a wet wiper for cleaning removable appliances that provides the one-step portability, convenience, performance, and desired sensory characteristics. U.S. Pat. Nos. 5,320,772 and 6,821,940 teach the use of fibrous wet wipers for cleaning foods, toys and food/child contact surfaces. The problem with this technology is that it does not address the specific needs required of an oral hygiene product for cleaning removable appliances. For such a product, it is necessary to include ingredients specific to oral care that deliver pleasant flavor and mouth refreshment, and that also remove/reduce plaque, calculus, stain and malodor. Thus, the present invention substantially departs from the conventional concepts and designs of the prior art, and provides a means to deliver improved benefits for the specific purpose of cleaning removable appliances without rinsing, while also providing portability in a one-step cleaning regimen.

BACKGROUND ART

U.S. Pat. Nos. 6,831,050, 6,821,940, 6,662,813, 6,557,568, 6,367,488, 6,345,634, 5,549,758, 5,705,461, 5,965,499, 5,500,143, 5,500,048, 5,498,295, 5,503,764, 5,997,654, 5,849,678, 5,749,924, 5,914,302, 5,879,470, 5,932,527, 5,972,857, 5,320,772, GB 2224425, WO 09701290A2, WO 09818352A1, WO 09850518A1, WO 09900026A1, WO 09900025A1, and WO 09856889A1.

BRIEF SUMMARY OF THE INVENTION

Accordingly, it is a principal object of the present invention to provide a method of cleaning oral debris from removable appliances with a wet wiper that does not require subsequent rinsing, brushing or soaking of the removable appliance.

It is another object of the present invention to provide a disposable wet wiper that may be used in lieu of a brush, ultrasonic cleaner, or a chemical soak.

It another object of the present invention to provide a disposable wet wiper that provides an immediate effect of refreshment to the user and replaces oral malodors with a pleasant flavor.

It is another object of the present invention to promote oral hygiene by providing a wet wiper, in a unit dose or bulk package, that can be used at any time or in any location without requiring any other auxiliary aids in the cleaning regimen.

It is another object of the present invention to provide a method for reducing bacteria on removable appliances.

Still another object of this invention is to provide a method for treating and storing removable appliances rendering the oral debris more amenable to removal during a subsequent cleaning process.

In accordance with the foregoing objectives, this invention provides a method for cleaning removable appliances with a wet wiper. The wet wiper comprises:
 (a) a water insoluble substrate; and
 (b) a physiologically acceptable cleansing composition comprising:
   (i) ethyl alcohol;
   (ii) a flavor;
   (iii) optionally, a nonionic surfactant;
   (iv) optionally, an anionic surfactant;
   (v) optionally, a chelating agent;
   (vi) optionally, a buffering salt pair;
   (vii) optionally, an antimicrobial, antiplaque agent;
   (viii) optionally, an anticalculus agent;
   (ix) optionally, a zinc salt;
   (x) optionally, a humectant;
   (xi) optionally, a preservative;
   (xii) optionally, a suds suppressor;
   (xiii) optionally, a sweetener;
   (xv) optionally, a water soluble polymer; and
   (xiv) water;
 wherein said cleansing composition has a pH of from about 3.0 to about 13.0 and is loaded onto the substrate at a loading factor of at least about 0.5 grams of composition per gram of dry substrate so that said substrate is wet by said composition, wherein said substrate releasably carries the cleansing composition.

DETAILED DESCRIPTION OF THE INVENTION

The wet wipers of the present invention typically comprise a water insoluble substrate and a physiologically acceptable cleansing composition. The methods of the present invention can be carried out by wiping the surface of the removable appliance with the wet wiper of the present invention. This invention effectively cleans dental appliances while not leaving behind a residue that may harm the user and/or have an objectionable taste. It does so as follows: first, the removable appliance is cleaned mechanically by the natural friction created by the wiping action of the wet wiper which is effective at removing gross material from the surfaces of the appliance. Second, the wet wiper serves as a compact delivery vehicle for a physiologically acceptable cleansing composition that enhances the ability of the wet wiper to additionally loosen and dislodge dental plaque as well as kill plaque bacteria and neutralize malodors. Third, residual cleansing composition remaining on the surfaces of the removable appliance will continue to inhibit bacterial growth and odor formation after the appliance is reinserted into the patient's oral cavity. And fourth, the wet wiper may also be used for storing removable appliances for short time periods (e.g., work breaks, snacks, meals). The removable appliance may be contacted with the wet wiper and stored in a sealed container (i.e., appliance storage case). Storing the removable appliance with the wet wiper prevents the loss of moisture from the appliance thereby keeping the adhered oral debris in a softened state and more amenable to removal by mechanical action.

DEFINITIONS

The term "removable appliance" means a prosthetic dental appliance removed from the patient's mouth when the appliance is cleaned. Removable appliance includes, but is not limited to, biteplates, dentures, partial dentures, orthodontic retainers, INVISALIGN® aligners (INVISALIGN®, custom manufacture of orthodontic appliances, dental laboratory services, is a registered trademark of Align Technology, Inc. (San Jose, Calif.)), RAINTREE-ESSIX appliances, mouthguards, sportsguards, nightguards, antisnoring devices, and TMJ splints.

The term "oral debris" means any matter accumulated on the surface of a removable appliance. This includes particulate and nonparticulate matter, organic and inorganic matter, and mineralized and nonmineralized matter. Oral debris includes plaque, pellicle, loosely adherent foodstuffs, stagnating saliva, stain, bacteria, and calculus.

The term "wet wiper" means a water insoluble substrate in and on which a cleansing composition is loaded. The wet wiper contains sufficient cleansing composition to make it wet, damp or moistened. That is the wiper has a loading factor of at least about 0.5 grams of cleansing composition per gram of dry substrate.

The term "releasably carrying" means that a cleansing composition is either in or on a water insoluble substrate and is readily releasable from the substrate by applying some force to the substrate. For example, wringing the substrate, or wiping a surface of a removable appliance.

The term "antimicrobial antiplaque agent" refers to a wide variety of substances including, but not limited to halogenated salicylanilides, halogenated carbanilides, halogenated bisphenols, alkylbenzoylacrylates, quaternary ammonium compounds, thiuram sulfides, dithiocarbamates, antibiotics, halogenated diphenyl ethers, halogenated anilides of thiophene carboxylic acids, chlorhexidines and certain flavor oils including thymol, eucalyptus, methyl salicylate, menthol, spearmint oil and peppermint oil.

The term "water insoluble" means the substrate does not dissolve or readily break apart upon immersion in water.

The term "physiologically acceptable" means that the wet wiper under conditions of intended use is safe and organoleptically tolerable in the oral cavity, having no significant side effects either orally or systemically when used as directed.

Article Substrate

A necessary ingredient of the present invention is that of a water insoluble substrate A wide variety of materials can be used as the substrate. The following nonlimiting characteristics are desirable: (i) sufficient wet strength for use, (ii) sufficient abrasivity, (iii) sufficient loft and porosity, (iv) sufficient thickness, and (v) appropriate size.

Nonlimiting examples of suitable insoluble substrates which meet the above criteria include nonwoven substrates, woven substrates, hydro-entangled substrates, air entangled substrates, foams, sponges and the like. Preferred embodiments employ nonwoven substrates since they are economical and readily available in a variety of materials. By nonwoven is meant that the layer is comprised of fibers which are not woven into a fabric but rather are formed into a sheet, particularly a tissue. The fibers can either be random (i.e., randomly aligned) or they can be carded (i.e., combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as ACRILAN® (ACRILAN®, acrylic fibers, is a registered trademark of Solutia inc. (St. Louis, Mo.)) and CRESLAN, and the acrylonitrile-based fiber, ORION; cellulose ester fibers such as cellulose acetate, ARNEL, and ACELE; polyamides such as Nylons (e.g., Nylon 6, Nylon 66, and Nylon 610); polyesters such as FORTREL® (FORTREL®, synthetic fibers, is a registered trademark of Fiber Industries Inc. (Shrewsbury)), KODEL, and DACRON, polyolefins such as polypropylene, polyethylene; polyvinyl acetate fibers and mixtures thereof.

Nonwoven substrates made from natural materials consist of webs or sheets most commonly formed on a fine wire screen from a liquid suspension of the fibers.

Substrates made from natural materials useful in the present invention can be obtained from a wide variety of commercial sources. Non-limiting examples of suitable commercially available paper layers useful herein include AIRTEX, an embossed airlaid cellulosic layer having a base weight of about 71 gsy, available from James River Corporation, Green Bay, Wis.; and WALKISOFT, an embossed airlaid cellulosic having a base weight of about 75 gsy, available from Walkisoft U.S.A., Mount Holly, N.C.

Non-woven substrates made from synthetic material useful in the present invention can also be obtained from a wide variety of commercial sources. Non-limiting examples of suitable non-woven layer materials useful herein include KEYBAK® 951V, a dry formed apertured material, containing about 75% rayon, about 25% acrylic fibers, and having a basis weight of about 43 gsy, available from Chicopee Corporation, New Brunswick, N.J.; KEYBAK® 1368, an apertured material, containing about 75% rayon, about 5% polyester, and having a basis weight of about 39 gsy, available from Chicopee Corporation, New Brunswick, N.J.; DURALACE® 1236, an apertured, hydro-entangled material, containing about 100% rayon, and having a basis weight from about 40 gsy to about 115 gsy, available from Chicopee Corporation, New Brunswick, N.J.; DURALACE® 5904, an apertured, hydro-entangled material, containing about 100% polyester, and having a basis weight from about 40 gsy to about 115 gsy, available from Chicopee Corporation, New Brunswick, N.J.

Most preferred for this invention are non-woven webs because such webs are generally less expensive to produce and have a more generally open surface for receiving and holding oral accumulations from the removable appliance. A preferred substrate of the present invention is SONTARA® 8868, a hydro-entangled material, with an open weave or perforated configuration, containing about 50% cellulose and about 50% polyester, and having a basis weight of about 60 gsy, available from Dupont Chemical Corp. Another preferred substrate of the present invention is a spunlace nonwoven material having a basis weight of 60 gsm comprising 50% rayon and 50% polyester available from Web Pro.

Viscoelastic substrates useful in the present invention include polyolefin, urethane, and silicone flexible foams. Specially formulated hydrophilic urethanes are free of PVC, latex, and solvents, which gives them durability, and biocompatibility. Nonlimiting examples of suitable foam materials useful in the present invention include MediSponge and Novapreme, hydrophilic polyurethane foams available from Lendell Inc., Saint Charles, Mich., and Capu-Cell polyurethane foams available from TMP Technologies, Niagara Falls, N.Y. Other foams with similar characteristics may also be used.

The substrate of the present invention can comprise two or more layers, each having a different texture and abrasiveness. The differing textures can result from the use of different combinations of materials or from the use of a substrate having a more abrasive side for debridement and a softer, absorbent side for gentle cleansing. In addition, separate layers of the substrate can be manufactured to have different colors, thereby helping the user to further distinguish the surfaces.

The substrate of the present invention may also comprise binders as known to the art. Suitable binders include latex binders; conform binders where the fibers comprise at least two polymers where one of the polymers has a melting point that is lower than the other; powdered polymeric binders where the polymeric powder has a lower melting point than the fibers comprising the substrate; and other binders as are known and used in the art.

The substrate of the present invention is not limited to any form, specific pattern, design or geometry. It may be made into a wide variety of shapes and forms including flat pads, thick pads, thin sheets, ball-shaped implements, irregularly shaped implements and patterns. It can also be of any size, including but not limited to circular, rectangular, square, and ellipsoidal, and the size can be selected as appropriate for the shape and size of the dental appliance to be cleaned, or chosen to provide a desirable visual appearance.

The wet wipers of this invention generally are intended as disposable items. As used herein, "disposable" is used in its ordinary sense to mean a wet wiper that is disposed or discarded after a single use.

The wet wiper is made by wetting the dry substrate with at least 0.5 grams of composition per gram of dry substrate. Preferably, the dry substrate is wetted with at least about 1.0 grams, and more preferably at least about 1.5 grams of composition per gram of the dry substrate. Preferably, the dry substrate is wetted with at most about 5.0 grams, more preferably at most about 4.0 grams of composition per gram of the dry substrate. A "loading factor" of 0.5 means that the dry substrate is wetted with 0.5 grams of composition per gram of dry substrate.

Physiologically Acceptable Cleansing Composition

The following components are used in the preparation of the preferred compositions herein.

(i) Flavor

A necessary ingredient of the present invention is a flavor. The flavor is an important feature of the cleansing composition. A good flavor enhances the acceptability of the product and favors the prospect of user compliance with good oral hygiene practice. Since residual amounts of the liquid carrier will remain on the surfaces of the removable appliance, the cleansing composition of this invention contains flavors to improve palatability and acceptance by the patient or consumer. In addition, flavors provide an aroma which will serve as a signal or sensory cue to the consumer and heighten their awareness and appreciation of the product's action. Flavors include essential oils and synthetic flavoring substances generally recognized as safe (GRAS ingredients) as outlined in the 21 CFR. Suitable flavors include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, cinnamaldehyde glycerol acetal known as CGA, propenyl guaethol, cinnamon, vanillin, cranberry, ethyl vanillin, thymol, linalool, heliotropine, 4-cis-heptenal, diacetyl, methyl-para-tert-butyl phenyl acetate, and mixtures thereof. Certain flavors such as thymol, eucalyptol, menthol, methyl salicylate, cinnamic aldehyde, peppermint oil, spearmint oil, wintergreen oil, and cinnamon oil can also act as antimicrobial agents in the compositions disclosed herein. Coolants may also be part of the flavor system. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as FRESCOLAT® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson et al., issued Jan. 23, 1979.

The preferred flavor is an essential oil mixture selected from the group consisting of spearmint, peppermint and mixtures thereof. It should be noted that the specific choice of this type of flavor is made on the basis that this class of flavor is a highly desirable flavor to the consuming public as representing and furnishing a fresh mouth feel in oral care products. More importantly, these are preferred because this flavor group comprises spearmint and/or peppermint essential oils, which provide excellent persistent flavor notes effective for residual odor masking.

A flavor is typically present in the present invention at levels of from about 0.001% to about 5%, preferably from about 0.002% to 2% and more preferably from about 0.003% to about 1% by weight of the cleansing composition.

(ii) Liquid Carrier

A necessary ingredient of the present invention is a liquid carrier. The liquid carrier is a solution of water and ethyl alcohol and may comprise from about 10% to about 95% of the cleansing composition, e.g., the cleansing composition may include as the liquid carrier a component of about 3% to 90% by weight ethyl alcohol and about 97% to 10% by weight water. Ethyl alcohol serves several functions in the cleansing composition including the solubilization of flavors and water insoluble antimicrobial agents, formula preservation, and enhancing flavor impact.

(iii) Surfactant

An optional ingredient of the present invention is a surfactant. A surfactant is a surface-active agent that lowers the surface tension of the carrier liquid so that it will more quickly wet out the surfaces of the removable appliance. In addition, the surfactant helps in dispersing, emulsifying and penetrating oral accumulations making them more amenable to removal by mechanical action. The surfactants employed in the invention are those surfactants which are reasonably stable through a pH range of 3.0 to 13.0 and are nontoxic and therefore suitable for use on appliances intended for use in the oral cavity. Although anionic, nonionic, cationic and zwitterionic surfactants are suitable for this invention, cationic and zwitterionic surfactants are not preferred due to their capacity to stain the oral cavity's hard tissues and adversely affect composition palatability. Persons skilled in the art are aware of this possibility and should incorporate these surfactants with these limitations in mind.

(iv) Anionic Surfactant

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate, sodium lauroyl sarcosinate and sodium coconut monoglyceride sulfonates are examples of anionic surfactants of this type. Mixtures of anionic surfactants can also be utilized. Certain anionic surfactants can also act as germicides in the compositions disclosed herein. A highly preferred anionic surfactant is sodium lauryl sulfate which has been shown in U.S. Pat. No. 4,992,259 to have antimicrobial properties.

(iv) Nonionic Surfactant

The water soluble nonionic surfactants utilized in this invention are commercially well known and have been safely used in pharmaceutical and oral care products for many years. Among the satisfactory nonionic surfactants that may be employed in the present invention are the condensates of 2 to 30 moles of ethylene oxide with sorbitan mono- and tri-$C_{10}$-$C_{20}$ alkanoic acid esters having a HLB of 8 to 15. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate. Although the Tweens may be employed in the present invention, they have a bitter taste and detract from the overall palatability of the cleansing composition.

Highly preferred water soluble nonionic surfactants are marketed under the trade name "PLURONIC®," which are polyoxamers, i.e., nonionic triblock copolymers composed of a central hydrophobic chain of polyoxypropylene (poly(propylene oxide)) flanked by two hydrophilic chains of polyoxyethylene (poly(ethylene oxide)). The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. PLURONIC® surfactants useful in the present invention are types F68, F108, and F127. These are virtually tasteless and odorless and compatible with a wide variety of formulating ingredients. PLURONIC® F-127 is the most preferred of the series having been formulated safely in mouthwashes for many years.

Another highly preferred water soluble nonionic surfactant is the ethoxylated hydrogenated castor oil, which has an ethoxylation number of about 35 to about 60, that is, it has an average of about 35 to about 60 ethoxy groups ($C_2H_5O$—) per castor oil molecule. Ethoxylated hydrogenated castor oil can be obtained by reacting hydrogenated castor oil with ethylene oxide. Ethoxylated hydrogenated castor oils are available from BASF, Mount Olive, N.J., USA under the tradename CREMOPHOR® RH. Particularly preferred are CREMOPHOR RH-40 (PEG-40 Hydrogenated Castor Oil with an ethoxylation number of about 40) and CREMOPHOR RH-60 (PEG-60 Hydrogenated Castor Oil with an ethoxylation number of about 60). Ethoxylated hydrogenated castor oils are virtually tasteless and odorless and compatible with a wide variety of formulating ingredients.

The surfactant or mixtures of compatible surfactants can be present in the present invention from about 0.1% to about 5.0%, preferably from about 0.3% to about 3.0% and most preferably from about 0.5% to about 2.0% by weight of the cleansing composition.

(v) Chelating Agent

An optional ingredient of the present invention is a chelating agent. Chelating or sequestering agents may be used in the present invention to assist in the removal of calculus, stain and plaque contained on the surfaces of the removable appliance. The preferred chelating agents herein are polyphosphate salts or organic polycarboxylic salts, e.g., sodium and/or potassium citrate, and/or sodium and/or potassium ethylenediaminetetraacetate. Other organic polycarboxylic acids such as citric, tartaric, malic, etc., acids can also be used. Complex phosphates can also be used, but are generally avoided due to regulatory considerations where phosphate levels are specifically forbidden or highly restricted. Typically, if used in the present invention, the chelant is present at a level of from about 0.0005% to about 3%, preferably from about 0.001% to about 0.5%, and more preferably from about 0.003% to about 0.2%, by weight of the cleansing composition. Chelant can maintain the efficacy of the formulas in the presence of hardness.

(vi) Buffer

Another optional ingredient of the present invention is a buffering agent. The pH of the present compositions is preferably adjusted through the use of buffering agents. Buffering agents, as used herein, refer to agents that can be used to adjust the pH of the compositions to a range of about 3.0 to about 13.0. Common buffer systems include phosphoric acid and sodium phosphate salts, or citric acid and sodium citrate. Suitable buffers for use in this invention include potassium and/or sodium carbonate, potassium and/or sodium bicarbonate, potassium and/or sodium hydroxide (hydrate), potassium and/or sodium citrate and/or potassium and/or sodium ortho-phosphate, citric acid-sodium citrate, phosphoric acid-sodium phosphate, sodium monobasic phosphate, sodium dibasic phosphate, acetic acid-sodium acetate, succinic acid-sodium succinate, aconitic acid-sodium aconitate and benzoic acid-sodium benzoate.

The pH is preferably not greater than about 13, and especially does not contain large amounts of buffer at higher pHs for consumer safety, especially when the compositions are not fully removed from items. Reserve alkalinity should be from about 0.01 to about 10, preferably from about 0.05 to about 7, and more preferably from about 0.1 to about 4. Similarly, the pH is not lower than about 3.0 and especially does not contain large amounts of buffer at lower pHs for consumer safety, especially when the compositions are not fully removed from items.

In the present invention, the level of buffer, is typically from about 0.0005% to about 5%, preferably from about 0.0015% to about 2.5%, and more preferably from about 0.0025% to about 1.5%, by weight of the cleansing composition.

(vii) Antimicrobial Antiplaque Agent

Another optional ingredient of the present invention is an antimicrobial antiplaque agent that destroys the bacteria that play a role in the etiology of plaque and cause oral malodors.

Quaternary ammonium compounds are among the most common of the cationic antimicrobial agents. In oral compositions, they are highly effective in promoting oral hygiene by inhibiting or reducing the number of plaque forming bacteria. Quaternary ammonium antibacterial agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethylhexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, Jun. 3, 1980 to Bailey which is incorporated herein by reference. The pyridinium compounds are the preferred quaternary ammonium compounds for use in the present invention, the most preferred being cetylpyridinium chloride, tetradecylpyridinium chloride or mixtures thereof. Quaternary ammonium antimicrobial agents are included in the present invention at levels of about 0.01% to about 0.5%, preferably from about 0.01% to below about 0.2%, more preferably from about 0.01% to about 0.15% by weight of the cleansing composition.

Useful water insoluble noncationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. Triclosan monophosphate is also a suitable water soluble antimicrobial agent. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, September 27, 1977 to Gieske et al., incorporated herein by reference. Specific antimicrobial agents include chlorhexidine, triclosan, triclosan monophosphate, and flavor oils such as thymol, eucalyptol, menthol, methyl salicylate, cinnamic aldehyde, peppermint oil, spearmint oil, wintergreen oil, and cinnamon oil.

The noncationic antimicrobial agent is used in the present invention in an effective antiplaque amount, typically about 0.01-5% by weight preferably about 0.03-1% and most preferably about 0.3-0.5% by weight of the cleansing composition.

(viii) Anticalculus Agent

Another preferred optional ingredient of the present invention is an anticalculus agent. Well known anticalculus agents in the dental art are the linear molecularly dehydrated polyphosphate salts being generally employed in the form of their wholly or partially neutralized water soluble alkali metal (e.g., potassium and preferable sodium) or ammonium salts, and any mixtures thereof. Representative examples include sodium hexametaphosphate, sodium tripolyphosphate, disodium diacid, trisodium monoacid and tetrasodium pyrophosphates, the corresponding potassium salts and the like.

Particularly desirable anticalculus agents are tetraalkali metal pyrophosphates, such as tetrasodium pyrophosphate, tetrapotassium pyrophosphate and mixtures thereof.

In the present invention, the level of anticalculus agent, when present, is typically from about 0.0005% to about 10%, preferably from about 0.0015% to about 5%, and more preferably from about 0.0025% to about 1.5%, by weight of the cleansing composition.

(ix) Zinc Salt

Another optional ingredient of the present invention is a zinc salt. Zinc salts have been used over the years in several oral care products, primarily to limit or prevent malodor. Examples of such oral care products include AIM® toothpaste, Breath Savers® mints, Lavoris® mouthwash, Viadent® mouthrinse, and Listermint.®

The literature in this field shows there are numerous reasons to add zinc salts to a wet wiper for cleansing removable appliances. Among those reasons is its efficacy as an anti-malodor agent. Two mechanisms of action are believed to be responsible for zinc's utility as an anti-malodor agent. The first is its ability to form insoluble salts with nucleophilic compounds such as valeric acid, hydrogen sulfide, mercaptans, etc., (i.e., volatile sulfur compounds, "VSCs") which typically cause oral malodor. U.S. Pat. No. 4,992,259; Pader, M, Oral Hygiene Products and Practice, Chapter 10, pg. 351. Additionally, the literature shows that zinc salts inhibit proteolysis by direct action on bacterial proteases, like cysteine and methionine proteases, thus reducing the amount of odor causing agents. Marsh, P D, J. Clin. Periodontal, 18(6): 462-467, 1991.

Zinc has also been shown to have antimicrobial efficacy. Here, its mode of action is believed to result from surfactant charge activity, resulting in disruption of membranes. Verran, J. Int. J. Cosmet. Sci., 13: 29-42, 1991, as well as inhibition of essential enzymes in glucose transport and catabolism. Cummins D. J. Clin. Periodontol, 18: 455-461, 1991; and Marsh, P D, J. Clin. Periodontal, 18(6); 462-467, 1991.

Antiplaque and antigingivitis efficacy is another attribute of zinc salts. Part of this activity may be a direct consequence of its antimicrobial efficacy. Further, zinc may reduce the rate of bacterial adherence to teeth. Harrap, G J, Saxton, C A, Best, J S, Archs. Oral. Bio., 29(2): 87-91, 1984; and Harrap, G J, Saxton, C A, Best, J S, J. Periodont Res., 18: 634-642, 1983. Zinc is also said to prevent the toxic effects that volatile sulfur compounds have on membrane permeability by preventing VSC penetration into epithelial cells. Pader, M, Oral Hygiene Products and Practice, Chapter 10, pg. 351-352.

Moreover, zinc has been associated with anticaries activity resulting from inhibition of the dissolutive process of caries by reversible adsorption on apatite. Ingram, G S, Edgar, W M, Adv. Dent. Res., 8(2): 158-65, 1994.

Finally, zinc salts are believed to also have anticalculus efficacy resulting from adsorption of zinc ion on apatite, thus restricting crystal growth. Ingram, G S, Edgar, W M, Adv. Dent. Res., 8(2): 158-65, 1994; Ingram, G S, Horay, C P, Stead, W J, Caries, Res., 26(4): 248-253, 1992 and Gilbert, R J, Ingram, G S, J. Pharm. Pharmacol., 40(6): 399-402, 1988.

Suitable zinc salts are well known in the art, and are those which freely ionize in an aqueous or hydroalcohol base. Suitable salts include inorganic, organic and water insoluble and water soluble zinc salts. Nonlimiting examples of suitable zinc salts that may be employed include: zinc oxide zinc stearate zinc tribromosalicylanilide zinc methionine sulfate zinc carbonate zinc tannate zinc caprylate zinc octoate zinc oleate zinc laurate zinc silicate zinc fluoride zinc acetate zinc formate zinc lactate zinc fumarate zinc iodide zinc ammonium sulfate zinc nitrate zinc bromide zinc phenol sulfonate zinc chloride zinc salicylate zinc chromate zinc sulfate zinc citrate zinc gluconate zinc dithionate zinc succinate zinc fluorosilicate zinc glycerophosphate zinc tartarate. Preferred salts are zinc chloride, zinc citrate, zinc oxide, zinc acetate, zinc stearate, zinc methionine sulfate, zinc phenol sulfonate, zinc sulfate, and zinc gluconate. The most preferred salts are zinc chloride, zinc sulfate, and zinc citrate.

Zinc salts may be included in the present invention at levels of 0.01% to about 2%, preferably from about 0.05% to about 0.7% and most preferably from about 0.1% to about 0.3% by weight of the cleansing composition.

(x) Humectant

Another preferred optional ingredient of the present invention is that of a humectant. Humectants such as glycerin, sorbitol and related polyols (hydrogenated starch hydrolyzates), propylene glycol, polyethylene glycols, and xylitol may be used in combination with ethyl alcohol in the composition as a substitute for water further reducing the water activity of the liquid carrier and making the liquid carrier self-preserving eliminating the need for a preservative. Humectants will also impart glossiness and sheen to the surface of the dental appliance as well as provide some lubricity. These compounds are readily familiar to those skilled in the art and many variations of these ingredients can successfully be employed by one skilled in the art with simple experimentation. Due to economic considerations, sorbitol and related polyols are preferred water substitutes comprising from about 5% to 40%, preferably from about 8% to 25%, by weight of the cleansing composition.

(xi) Preservative

Another optional ingredient of the present invention is a preservative. Formulating the present compositions at high pH reduces the tendency for biological growth of contaminants, such as bacteria, fungi, or molds. Similarly, in compositions with acidic or neutral pH, biological growth of contaminants, such as bacteria, fungi, or molds may also be an issue. However, preservatives can help insure the lack of biological growth through contamination in making or in use. Preservatives may be present in a cleansing composition of any pH (e.g., acidic, neutral or basic). One illustrative preservative is Suttocide A, available from Sutton Laboratories. Another illustrative preservative is methyl paraben. Still another illustrative preservative is propyl paraben.

Preservatives, when used in the present invention, are typically present at levels from about 0.001% to about 5%, preferably from about 0.002% to about 2%, and more preferably from about 0.003% to about 1%, by weight of the cleansing composition.

(xii) Suds Suppressor

Another optional ingredient of the present invention is a suds suppressor.

The amount of suds suppresser can be tailored in conjunction with the type and level of surfactant used and foam level desired. Suitable silicone suds suppressors are available from suppliers, such as DC-4270 and DC2-4242 available from Dow Corning.

Suds suppressor, when used in the present invention is typically at levels from about 0.001% to about 5%, preferably from about 0.002% to about 2%, and more preferably from about 0.003% to about 1%, by weight of the cleansing composition.

(xiii) Sweetener

Another optional ingredient of the present invention is that of a sweetener. Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. Sweeteners, when used in the present invention, are typically present at levels from about 0.001% to about 2%, and preferably from about 0.002% to about 1%, and most preferably from about 0.003% to 0.5% by weight of the cleansing composition.

(xiv) Antioxidant

Another optional ingredient of the present invention is an antioxidant. The use of surfactants, and especially soaps, may be complicated by development of off-odors and/or yellowing of the compositions in which they appear. These undesirable properties are believed to be caused by complex side reactions initiated by the reaction of oxygen, with, for example, any polyunsaturated components of any fatty acid present. These results can be avoided, or minimized, by avoiding contact with air, or by controlling the quality of the fatty acid stock so that the amount and type of polyunsaturates are minimized, or by minimizing oxygen sensitive components, and/or by the addition of chelants and/or antioxidants.

It has been found, that the addition of tocopherols (e.g., Vitamin E, or tocopherol acetates) in alkaline formulations is advantageous, as they do not degrade, nor do they impart a strong color. They inhibit the development of off-odors for extended periods of time so that the need for masking scents is minimized, or eliminated, particularly for oleic acid stocks of high quality, as described above. The use of butylated phenols, such as BHT and BHA is also useful, but their effectiveness appears more limited and they can impart stronger colors to the compositions. Other food grade antioxidants such as Vitamin C, sorbates, and sulfites, are desirable to prevent deterioration of the compositions by the action of oxygen, but care must be taken since vitamin C can suffer color degradation and sulfites can cause odor problems. Sulfites also have been the target of potential health concerns.

Antioxidants when used in the present invention, are typically present at levels from about 0.001% to about 5%, preferably from about 0.002% to about 2%, and more preferably from about 0.003% to about 1%, by weight of the cleansing composition.

(xv) Water Soluble Polymers

Another optional ingredient of the present invention is a water-soluble polymer. Water-soluble polymers may be used to affect the qualitative tactile impression of the wet wiper by increasing the viscosity of the cleansing composition and improving the "feel" of the wet wiper which comes in contact with the users' hands. Residual water soluble polymer remaining on the surfaces of the removable appliance may also provide lubricity/slipperiness which is detected by the user upon reinsertion of the appliance in their mouth. Water-soluble ingredients include but are not limited to sodium carboxymethyl cellulose, polyvinyl pyrrolidone, methyl cellulose, polyvinyl alcohol, hydroxy propyl methyl cellulose, xanthan gum, hydroxyethyl cellulose, carrageenan and mixtures thereof.

Water-soluble polymers when used in the present invention are typically present at levels from about 0.001% to about 2%, preferably from about 0.005% to about 1%, and more preferably from about 0.01% to about 0.5% by weight of the cleansing composition.

Wet Wiper Packaging Enclosure

The packaging enclosure for the wet wiper must protect the product from loss of flavor, water, alcohol, and other volatiles, if present. It must not interact with the product with resultant adverse effects on either the cleansing composition or package properties. It must effectively reduce permeation of oxygen, which can negatively impact the components of the cleansing composition and overall product acceptability. And from a cosmetic point of view, it should show the product off to its maximum. Packaging for holding a water insoluble substrate loaded with the cleaning composition can be of any suitable form. A sealed envelope can be used to hold a wet wiper saturated with the cleaning composition until the time of use. Such an envelope is preferably composed of a plastic material impermeable to air and the vapors of the ingredients comprising the cleaning composition. A preferred package is a resealable container that can hold several wet wipers loaded with the cleaning solution and that is essentially airtight to prevent the evaporation of the volatile components of the cleaning composition. Such a resealable container can be hard or soft with a resealable opening which a wet wiper is pulled. Such containers are commercially available from a variety of sources. The containers desirably contain from about 10 to about 500 wet wipers per container, and more desirably contain from about 30 to about 200 wet wipers per container. The wet wipers within a container package may be arranged in a variety of ways, including, but not limited to interfolded, C-folded, stacked, and so forth.

Resealable label flaps of peel and seal labels are commonly used for packaging wet wipers. The product packages are generally constructed from a thin, liquid-impervious material that has an opening over which the label flap is removably adhered. Typically, the label flap is a strip of flexible film or semi-rigid thermoplastic material having a removable pressure-sensitive adhesive applied to one surface of the label. The removable adhesive creates a generally airtight seal around the package opening to prevent the packaged wet wipers from drying out during storage.

In one preferred embodiment of the present invention the wet wiper substrate has dimensions, approximately 5×4 inches and is able to be folded by four fold lines into a rectangular folded form measuring approximately 1¼×1¾ inches which is closely received by the envelope. The packaging enclosure is a tear-open, rectangular envelope, of pocket-sized dimensions; approximately 3¼×2¼ inches consisting of a foil based laminated plastic of the type conventionally used in the art and capable of being hermetically sealed.

The manner of making and using the present invention will be illustrated further by the following detailed examples.

Example 1

A wet wiper was prepared using the following procedure. First, a cleansing composition was prepared according to the formula that follows:

| Ingredient | (% w/w) | Ingredient Function |
|---|---|---|
| Water | QS 100 | Component of liquid carrier |
| Grain Alcohol (151 proof) | 48.00 | Component of liquid carrier |
| Glycerin | 3.00 | Humectant |
| Keltrol T (xantham gum) | 0.03 | Water soluble polymer |
| Spearmint/peppermint oil | 0.2 0 | Flavor |

The above composition is formulated by making a first solution of the grain alcohol and flavor. In a separate vessel, xantham gum is dispersed in glycerin. The xantham gum/glycerin mixture is slowly added to the formula amount of water while stirring vigorously. The alcoholic solution is then combined with the aqueous solution. The pH of the final solution is approximately 5.5.

A substrate was prepared by cutting a 5×4 inch section from spunbonded Sontaro 8868 rollstock obtained from DuPont Chemical Corp. A partially sealed envelope was prepared to receive the wet wiper by first cutting a 6½×2½ section of a laminated packaging film, Glenroy EFS 008. The cut film was folded once and then sealed on three sides. The substrate is able to be folded by four fold lines into a rectangular folded form measuring approximately 1¼×1¾ inches and weighing approximately 0.8 grams which is then received by the envelope. Four grams of the liquid cleansing composition is added to the folded substrate contained in the envelope. The envelope is then sealed.

Example 2

A wet wiper was prepared using the following procedure. First, a cleansing composition was prepared according to the formula that follows:

| Ingredient | (% w/w) | Ingredient Function |
|---|---|---|
| Water | QS 100 | Component of liquid carrier |
| Grain Alcohol (151 proof) | 25.00 | Component of liquid carrier |
| Tetrapotassium pyrophosphate | 1.90 | Anticalculus agent |
| Disodium ethylenediaminetetraacetic acid | 0.05 | Chelating agent |
| Sorbitol (70% solution) | 10.00 | Humectant |
| Peppermint oil | 0.15 | Flavor |

The above composition is formulated by making a first solution an aqueous solution by combining water, sorbitol, tetrapotassium pyrophosphate and disodium ethylenediaminetetraacetic acid. An alcoholic solution of the grain alcohol and peppermint oil is prepared separately. The alcoholic solution is added to the aqueous solution and mixed. The pH of the final solution is approximately 10.6.

A substrate was prepared by cutting a 6×9 inch sections from a 100% polyester spun lace nonwoven wipe available from Green Bay Nonwoven. An airtight resealable container was prepared to receive 50 folded wet wipers. 200 grams of the cleansing composition is added to the folded substrates contained in the package. The package is then sealed.

Example 3

A wet wiper was prepared using the following procedure. First, a cleansing composition was prepared according to the formula that follows:

| Ingredient | (% w/w) | Ingredient Function |
|---|---|---|
| Water | QS 100 | Component of liquid carrier |
| Grain alcohol (151 proof) | 21.93 | Component of liquid carrier |
| Sorbitol (70% solution) | 10.00 | Component of liquid carrier |
| Sodium lauryl sulfate | 0.1 | Surfactant, antimicrobial |
| Glacial acetic acid | 0.02 | Buffer |
| Sodium acetate | 0.03 | Buffer |
| Zinc chloride | 0.22 | Neutralize malodors |
| Poloxamer 407 | 0.2 | Surfactant |
| Peg-40 hydrogenated castor oil | 0.4 | Surfactant |
| Dow antifoam FG10 | 0.2 | Suds suppressor |
| Spearmint/peppermint oil | 0.4 | Flavor |

The above composition is formulated by making a first solution of water, sorbitol, glacial acetic acid, sodium acetate, and zinc chloride. A second solution is made by combining the grain alcohol, polysorbate 20, poloxamer 407, sodium lauryl sulfate, Dow antifoam FG10 and flavor. This alcoholic solution is then added to the first solution and the resulting solution is mixed. The final pH of the solution is adjusted to 3.5-4.0 using 0.1N HCl.

A substrate was prepared by cutting four inch circular shapes from a spunlace nonwoven substrate having a basis weight of 60 gsm comprising 50% rayon and 50% polyester obtained from Web Pro Inc. A resealable hard plastic case was filled with twenty circular shapes and eighty grams of the cleansing composition is added to the substrate laying flat in the plastic case. The plastic case is then sealed.

Example 4

A pharmaceutical sales representative undergoing orthodontic treatment with Invisalign is preparing for a meeting with a physician client. Prior to the meeting the sales representative removes his/her removable orthodontic appliance (aligner) to wipe it with a premoistened wipe of Example 3. The premoistened wipe removes accumulated oral debris as well as neutralizes any malodors which could have been detected by the physician. The sales representative then reinserts the aligner in his mouth and joins his client for a meeting.

Example 5

An office worker wearing a Hawley retainer is preparing to take a lunch break. The worker removes the Hawley retainer and wraps it in a premoistened wipe of Example 1. The worker places the wrapped retainer in a plastic dental case. During lunch, the low pH premoistened wipe keeps the dental plaque hydrated and in a softened state making it more amenable to mechanical removal. After returning from lunch, the worker removes the retainer from the dental case and wipes all surfaces and parts of the retainer and then inserts it their mouth. The used premoistened wipe is discarded.

Example 6

A student wearing an Essix retainer is walking between classes and needs to grab a snack. The student removes his Essix retainer and places his appliance in his pocket. After finishing a quick snack and drink, the student retrieves his retainer. Using a premoistened wipe of Example 1 he wipes all surfaces of his retainer removing accumulated oral debris. He also freshens his appliance in the process of cleaning it, transferring the minty flavor from the wipe onto his retainer, before reinserting it into his mouth, to enjoy a burst of flavor refreshment. He then discards the wipe and heads into his next class.

Example 7

A camper wearing a removable partial denture is hiking in the back mountains with no access to running water. During a meal, she feels food particles around the area of her partial appliance. She removes the partial appliance and places it on the picnic bench to finish her lunch. After lunch she uses a premoistened wipe of Example 1, to wipe all surfaces of the appliance removing the accumulated debris and odors before reinserting it in her mouth to have the benefit of its clean feeling.

As will be understood by those with ordinary skill in the art, the present invention may be modified or varied in many ways and embodied in other specific forms without departing from the spirit or essential characteristics of the present invention. It is to be understood that no limitation with respect to the specific embodiments illustrated is intended or should be inferred. Modifications and variations are not to be regarded as a departure from the spirit and scope of the present subject matter, and all such modifications and variations, equivalents and alternatives, and others, are intended to be included within the scope of the present invention. Accordingly, for an understanding of the scope of the invention, reference should be made to the appended claims.

What is claimed is:

1. A wet wiper consisting essentially of:
   a. a water insoluble substrate; and
   b. a physiologically acceptable cleansing composition, said cleansing composition consisting essentially of: a solution of water and a flavorant, wherein said water is up to about 97% by weight of said cleansing composition; and said flavorant is about 0.001% to about 5% by weight of said cleansing composition; and wherein said flavorant is selected from the group consisting of oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, cinnamaldehyde glycerol acetal (CGA), propenyl guaethol, cinnamon, vanillin, cranberry, ethyl vanillin, thymol, linalool, heliotropine, 4-cis-heptenal, diacetyl, methyl-para-tert-butyl phenyl acetate, and mixtures thereof.

2. The wet wiper of claim 1, wherein said flavorant is selected from the group consisting of spearmint oil, peppermint oil and mixtures thereof.

* * * * *